(12) United States Patent
Thyzel

(10) Patent No.: US 8,715,273 B2
(45) Date of Patent: May 6, 2014

(54) METHOD AND DEVICE FOR REMOVING AND/OR INHIBITING OF MOLECULAR STRUCTURES AND/OR CELLS FROM OR AT HUMAN OR ANIMAL TISSUE

(76) Inventor: Reinhardt Thyzel, Heroldsberg (DE)

( * ) Notice: Subject to any disclaimer, the term of this patent is extended or adjusted under 35 U.S.C. 154(b) by 1871 days.

(21) Appl. No.: 11/944,597

(22) Filed: Nov. 23, 2007

(65) Prior Publication Data

US 2008/0114341 A1    May 15, 2008

Related U.S. Application Data

(63) Continuation-in-part of application No. 11/553,782, filed on Oct. 27, 2006, now abandoned, which is a continuation-in-part of application No. PCT/EP2005/000360, filed on Jan. 15, 2005.

(30) Foreign Application Priority Data

Apr. 30, 2004   (DE) .......................... 10 2004 021 754

(51) Int. Cl.
    *A61B 18/20*   (2006.01)
(52) U.S. Cl.
    USPC .................................. 606/6; 606/4; 128/898
(58) Field of Classification Search
    USPC ...................... 606/4–6, 9, 13–16; 604/19–28; 607/134–137; 128/898
    See application file for complete search history.

(56) References Cited

U.S. PATENT DOCUMENTS

| | | | |
|---|---|---|---|
| 4,652,092 A | 3/1987 | Schroder et al. | |
| 4,702,245 A | 10/1987 | Schroder et al. | |
| 4,733,400 A | 3/1988 | Thyzel et al. | |
| 4,911,160 A | 3/1990 | Thyzel | |
| 5,000,751 A | 3/1991 | Schroder et al. | |
| 5,204,331 A | 4/1993 | Nishi et al. | |
| 5,213,569 A * | 5/1993 | Davis .............................. | 604/22 |
| 5,258,992 A | 11/1993 | Thyzel | |

(Continued)

FOREIGN PATENT DOCUMENTS

| | | |
|---|---|---|
| JP | 2001-525199 | 12/2001 |
| WO | WO 89/12093 A1 | 12/1989 |
| WO | WO 2005/107665 A1 | 11/2005 |

OTHER PUBLICATIONS

Thyzel, ISR of WO 2005/107665 A1, Nov. 17, 2005.

*Primary Examiner* — Ahmed Farah
(74) *Attorney, Agent, or Firm* — The Law Office of James E. Ruland, PLC

(57) ABSTRACT

One exemplary method for removing and/or inhibiting unwanted molecular structures and/or cells from or at human or animal tissue, can include the steps of
a) supplying fluid medium so that the fluid medium is adjacent to or covers the molecular structures and/or cells that are to be removed and/or inhibited,
b) generating pressure pulses in the fluid medium, wherein preferably each pressure pulse comprises a pressure current and/or a pressure wave and/or a shock wave and/or wherein preferably the pressure pulses have the form of a pressure jet of the fluid medium that is or can be directed onto the molecular structures and/or cells, and/or exhibit at least one preferential direction or main propagation direction,
c) removing the molecular structures and/or cells from the tissue by the impacting pressure pulses and/or inhibiting molecular structures and/or cells which remain at the tissue by the impacting pressure pulses,
d) wherein the pressure pulses are so formed or selected that during removing and/or inhibiting of the molecular structures or cells no hole or comparable damage is produced in the adjacent tissue by the pressure pulses.

23 Claims, 2 Drawing Sheets

(56) References Cited

U.S. PATENT DOCUMENTS

| | | | |
|---|---|---|---|
| 5,322,504 A * | 6/1994 | Doherty et al. | 606/167 |
| 5,324,282 A | 6/1994 | Dodick | |
| 5,591,184 A * | 1/1997 | McDonnell et al. | 606/167 |
| 5,865,790 A * | 2/1999 | Bair | 604/35 |
| 5,906,611 A | 5/1999 | Dodick et al. | |
| 6,299,591 B1 | 10/2001 | Banko | |
| 6,322,557 B1 | 11/2001 | Nikolaevich et al. | |
| 6,887,269 B1 | 5/2005 | Hampp et al. | |
| 7,252,662 B2 * | 8/2007 | McArdle et al. | 606/5 |
| 2004/0158236 A1 | 8/2004 | Thyzel | |
| 2004/0167504 A1 | 8/2004 | Thyzel | |
| 2006/0173446 A1 * | 8/2006 | Dacquay et al. | 606/6 |
| 2007/0043340 A1 | 2/2007 | Thyzel | |
| 2007/0049862 A1 | 3/2007 | Thyzel | |
| 2007/0223862 A1 | 9/2007 | Thyzel | |

* cited by examiner

METHOD AND DEVICE FOR REMOVING AND/OR INHIBITING OF MOLECULAR STRUCTURES AND/OR CELLS FROM OR AT HUMAN OR ANIMAL TISSUE

REFERENCE TO RELATED APPLICATIONS

This application is a continuation-in-part of U.S. patent application Ser. No. 11/553,782 filed on Oct. 27, 2006 which is a continuation-in-part of PCT Application PCT/EP2005/000360 filed on Jan. 15, 2005 and claiming priority to German Patent Application No. 10 2004 021 754.8 filed on Apr. 30, 2004, the entire disclosures of which are hereby incorporated by reference.

TECHNICAL FIELD OF THE INVENTION

The invention relates to a method and to a device each for removing and/or inhibiting unwanted molecular structures and/or cells from or at human or animal tissue or for preventing or reducing proliferation or migration of epithelial cells at the inside of a lens-capsule bag of a human or animal eye.

BACKGROUND OF THE INVENTION

In opthalmology a known and frequently employed surgical procedure is to replace an eye's natural lens by an artificial (synthetic) one ("intraocular lens"). During this surgical intervention the natural lens is removed from its lens-capsule bag (explantation), after which an intraocular lens is inserted (implantation) into the remaining lens-capsule bag (capsula lentis). The explantation of the natural lens in practice involves destruction and extraction of the lens tissue (phacolysis), in general by phacoemulsification, during which the lens is emulsified (liquefied) by shock waves generated by means of an ultrasonic probe or a laser (photolysis) and is then removed by suction. The synthetic intraocular lens can be a prefabricated, rigid body mounted in the capsule bag by way of a supporting means (haptic device), but can also be a soft, yielding body or even be injected into the capsule bag as a free-flowing mass. When a flexible or yielding intraocular lens is used, it can accommodate—i.e., adjust its optical focal length—just as the natural lens does, by way of the ciliary muscles and the zonular fibres as well as the lens-capsule bag. The use of folding lenses or injectable lenses enables the surgical incision to be reduced, in practice to only 3 mm or even less. For the intraocular lens it is customary to use polymer materials that are transparent in the visible spectrum, in particular polymethyl methacrylate (PMMA) or silicone (polysiloxane elastomer) or acrylic.

Replacement of the natural eye lenses by a synthetic intraocular lens is at present employed only to eliminate a cataract, i.e. a cloudy lens. However, other cases for application are also possible, although more rarely encountered in practice: for example, an intraocular lens can be employed to adjust or correct the optical focal length, e.g. in cases of short-sightedness (myopia) or far-sightedness (hyperopia), or after accidents or injuries to the lens in which the lens-capsule bag itself is not irreparably damaged.

The document U.S. Pat. No. 5,324,282 A discloses a surgical instrument in the form of a needle for destroying tissue, which is designed to remove cataracts in optical surgery, i.e. to remove the lens of the eye by photolysis. This known instrument comprises a tubular outer wall with a longitudinal axis and a free end, as well as an optical fibre from a laser and an aspiration channel, each of which is longitudinally oriented and passes through the interior of the needle as far as its free end. At the free end of the needle a target made of titanium (Ti) is disposed, separated by some distance from the free end of the laser fibre, the fibre and the target being adjusted with respect to one another so that the laser beam from this fibre strikes the target. At the free end of the needle is also provided a tissue-aspiration port, disposed at an angle and laterally offset, into which the aspiration channel opens and which is disposed immediately adjacent to the target and the space between the end of the laser fibre and the target. By way of a suction pump a vacuum is created in the aspiration channel, by means of which the tissue to be destroyed is sucked up to the aspiration port and fractured, after which the individual fragments of the tissue are sucked away through the aspiration channel. When the tissue is in contact with or has been sucked against the tissue-aspiration port by the low pressure, laser pulses are shot out of the laser fibre and onto the target, the energy in these pulses being sufficient to produce an optical breakdown at the target material and hence generate a shock wave that strikes the tissue at the tissue-aspiration port and tears it into small pieces, which are then sucked away through the aspiration channel. The laser light is preferably generated with a neodymium-YAG laser and has a wavelength of 1,064 nm. The laser pulses have a pulse duration of 8 ns and a pulse repetition rate of 20 pulses per second. Hence the laser energy is 100 mJ per second and the energy of each pulse, 5 mJ. Furthermore, there can also be provided within the needle a longitudinally oriented irrigating tube to conduct flushing fluid through an outlet disposed at the side.

The document U.S. Pat. No. 5,906,611 A discloses a further development of the instrument known from U.S. Pat. No. 5,324,282 A, in which the target has a stepped structure, such that each step has two surfaces, one of which is oriented perpendicular to the needle axis and the other parallel thereto; the sequence of steps rises from an outer side, at the outside wall of the needle, towards the tissue-aspiration port. As a result, in each step zone of the target, as the target material evaporates the shock wave thus produced is not blocked by another part of the target in the direction towards the aspiration port. With a neodymium-YAG laser pulses can be produced with repetition rates between 2 and 50 pulses per second and pulse energies between 2 and 15 mJ. The pulse duration can be set between 8 and 12 ns. Preferably the pulse repetition rate is set at between 2 and 6 pulses per second and the pulse energy, between 6 and 10 mJ. For a cataract operation between 200 and 800 pulses or shots are used.

A laser handpiece constructed like those in U.S. Pat. No. 5,324,282 A and U.S. Pat. No. 5,906,611 A, together with a digital control and supply device that comprises a laser for the laser pulses as well as a venturi pump for aspirating the tissue parts, has for years been successfully marketed by the firm of A.R.C. Laser GmbH and was successfully employed in a large number of operations. Here aspiration occurs by way of the laser handpiece and irrigation with an electrolytic flushing solution (BSS) is done by way of a second instrument, in a bimanual technique. The product is sold under the name "Lyla/Pharo". For the actual eye operation employing this known device, various surgical techniques are used.

One problem with surgical explantation or phacolysis of the natural eye lens and the subsequent implantation of an artificial intraocular lens is the subsequent growth and proliferation of the epithelial cells that constitute the epithelium covering the inner surface of the lens-capsule bag. During this postoperative complication the newly formed epithelial cells migrate around the inserted artificial lens or even into it, eventually obscuring vision through the lens. This phenomenon is referred to as posterior capsule opacification (PCO), and when it follows a cataract operation it is also called a secondary cataract.

To alleviate this problem of postoperative proliferation of the epithelial cells in the capsule bag, various solutions have been suggested and employed. These can be subdivided as follows:
1. The removal of epithelial cells from the inner surface of the capsule bag during or after explantation of the eye lens and before implantation of the intraocular lens;
2. Preventing growth of the epithelial cells of the lens-capsule bag after implantation of the intraocular lens; and
3. Producing a hole or tear in the capsule bag by means of a laser, as a result of which the tissue of cells forming the epithelium is likewise torn apart (photodisruption, capsulotomy).

The removal of the epithelial cells is undertaken either by taking them away with a surgical instrument, such as a needle, or else chemically by applying substances toxic to cells or biochemically by antibodies.

So that after implantation of an intraocular lens the growth of remaining epithelial cells of the lens-capsule bag over the intraocular lens can be prevented or at least minimized, various measures are known, for example the use of special intraocular lenses, the surfaces of which are provided with structures such as pits or projections over which the epithelial cells cannot very easily grow, or are coated with growth-inhibiting cytotoxic substances; alternatively, growth-inhibiting cytotoxic substances can be implanted in the capsule bag itself, or an implant with photoactivatable immobilising substances can be inserted, as proposed in DE 199 55 836 C1. In the case of the opthalmological implant according to DE 199 55 836 C1 the pharmaceutical cytotoxic agent is released by photoactivation at a later time following the operation, at the earliest after the wound has completely healed, so as to kill off the epithelial cells on the lens and prevent the growth of new epithelial cells there. The chemical or biochemical removal of lens epithelial cells and prevention of their proliferation is described in EP 0 372 071 B1. The chemical removal of lens epithelial cells is furthermore described in Patent Abstracts of Japan 04352719 A.

A good survey of the known methods and devices for removing epithelial cells from the lens-capsule bag or of methods and substances to prevent growth of the epithelial cells can be found in the printed documents DE 199 55 836 C1 and EP 0 372 071 B1.

A fundamental problem associated with the known methods and apparatus for removing the epithelial cells by means of or during a surgical intervention resides in the fact that in no case have the epithelial cells been completely removed, in particular because certain places, e.g. along the equator and immediately behind the iris, are not readily accessible to the surgeon and because the chemical agents that are used ought not to be too aggressive on account of the danger of also damaging the capsule bag and adjacent eye regions, as well as the problem that wound healing may be impaired. However, if epithelial cells remain in the lens capsule, the risk of proliferation is always present.

SUMMARY OF THE INVENTION

A new method and a new device for removing and/or inhibiting unwanted molecular structures and/or cells from or at human or animal tissue is disclosed. In particular, a new method and a new device for preventing or reducing proliferation or migration of epithelial cells at the inside of a lens-capsule bag of a human or animal eye, in which the above-mentioned disadvantages in the state of the art are at least partially alleviated or entirely avoided, is disclosed.

The invention is based on the consideration that for the detaching (or: removing, carrying away, detaching, separating, forcing off) of cells or molecular structures from human or animal tissue, in particular of the epithelial cells from the inner wall of the lens-capsule bag or pathogenic microorganisms such as biofilms from tissue such as mucosa in noses or sinuses, pressure pulses in a fluid medium (a liquid) should be used. In particular this can be achieved by filling the lens-capsule bag or other hollow body space at least partly, but definitely in the region of the cells/structures that are to be removed, with said liquid.

The invention is based on the further consideration that it is also possible to inhibit the cells or molecular structures by means of pressure pulses in the fluid medium while they remain at the tissue, in particular in order to prevent proliferation or migration of the epithelial cells at the eye's lens-capsule bag to inhibit the epithelial cells at the wall of the lens-capsule.

Inhibiting means that the cells or molecular structures are affected or damaged by the pressure pulses to such an extent that they cannot grow or multiply any more or that, in other words, the cells become pignotic or inactive. Inhibited cells remaining at the tissue such as the lens-capsule bag may in some cases even form a barriere for other cells such as epithelial cells.

Both processes, detaching as well as inhibiting of the molecular structures or cells, can be used alone or also in combination, for instance at different regions of the tissue.

In both processes, detachment and inhibiting of the molecular structures or cells, the pressures and/or the energy and the impulse transmitted by or through the medium are adjusted regarding their time course in such a way that although the cells or molecular structures are separated (or: carried away, detached, removed) from the tissue or damaged while remaining at the tissue, the tissue is not otherwise damaged; in particular, the tissue remains intact and no hole or tear is produced in the tissue by the fluid medium impacting against it.

Here a pressure pulse should be understood to be a temporally delimited pressure elevation, in particular a pressure current or pressure wave or shock wave, which spreads out within the fluid medium as far as the cells or molecular structures. In this process, in addition to energy transport and impulse transport, as in the case of a wave, material transport can also occur as in the case of a current or a pressure jet.

A method for removing and/or inhibiting unwanted molecular structures and/or cells from or at human or animal tissue, according to the invention comprises the steps of
a) supplying fluid medium so that the fluid medium is directed to or is adjacent to or covers the molecular structures and/or cells that are to be removed and/or inhibited,
b) generating pressure pulses in the fluid medium, wherein preferably each pressure pulse comprises a pressure current and/or a pressure wave and/or a shock wave and/or wherein preferably the pressure pulses have the form of a pressure jet of the fluid medium that is or can be directed onto the molecular structures and/or cells, and/or exhibit at least one preferential direction or main propagation direction,
c) removing the molecular structures and/or cells from the tissue by the impacting pressure pulses and/or inhibiting molecular structures and/or cells which remain at the tissue by the impacting pressure pulses,
d) wherein the pressure pulses are so formed or selected that during removing and/or inhibiting of the molecular structures or cells no hole or comparable damage is produced in the adjacent tissue by the pressure pulses.

The unwanted molecular structures and/or cells can be in particular epithelial cells and/or pathogenic microorganisms like bacteria or fungi. The human or animal tissue can be tissue inside of or a wall of a lens-capsule bag of a human or animal eye, inside of human or animal nose or sinuses or in general inside of hollow area of human or animal body. A preferred use is during or after a cataract operation at the eye by which the risk of a secondary cataract or PCO is significantly reduced.

A method for preventing or reducing proliferation or migration of epithelial cells (or: epithelial tissue) at the inside (or: the inwardly directed surface) of a lens-capsule bag of a human or animal eye according to the invention comprises the steps of
a) generating pressure pulses in a fluid medium within the lens-capsule bag, such that the fluid medium is adjacent to or covers the epithelial cells, which pressure pulses impact on the epithelial cells,
b) detaching epithelial cells from the wall of the lens-capsule bag and/or inhibiting epithelial cells which remain at the wall of the lens-capsule bag by the impacting pressure pulses, so that the detached or inhibited epithelial cells are prevented from proliferating or migrating at the inside of the lens-capsule bag,
c) wherein the pressure pulses are so formed or selected that, during detaching or inhibiting of the epithelial cells, no hole or comparable damage is produced in the wall of the lens-capsule bag by the pressure pulses.

A device for removing and/or inhibiting unwanted molecular structures and/or cells from or at human or animal tissue, comprises
a) means for supplying or introducing fluid medium so that the fluid medium is adjacent to or covers the molecular structures and/or cells that are to be removed and/or inhibited,
b) means for generating pressure pulses in said fluid medium, wherein preferably each pressure pulse comprise a pressure current and/or a pressure wave and/or a shock wave and/or the pressure pulses preferably have the form of a pressure jet of the fluid medium that is or can be directed onto the molecular structures and/or cells, and/or exhibit at least one preferential direction or main propagation direction,
c) wherein the pressure pulses are so formed or selected that
c1) the molecular structures and/or cells can be or are removed or inhibited by the impacting pressure pulses, and at the same time
c2) during removing or inhibiting of the molecular structures and/or cells no hole or comparable damage is produced in the tissue, in particular by the pressure pulses.

A device or apparatus for preventing or reducing of proliferation or migration of epithelial cells at the inside of a lens-capsule bag of a human or animal eye according to the invention comprises
a) means for generating pressure pulses in a fluid medium within the lens-capsule bag, such that the fluid medium is adjacent to or covers the epithelial cells,
b) wherein the pressure pulses are so formed or selected
b1) that epithelial cells can be or are detached from the wall of the lens-capsule bag by the impacting pressure pulses and/or that epithelial cells which remain at the wall of the lens-capsule bag can be or are inhibited by the impacting pressure pulses, and, at the same time,
b2) no hole or comparable damage is produced in the wall of the lens-capsule bag by the pressure pulses.

In another embodiment a device for removing and/or inhibiting unwanted molecular structures and/or cells from or at human or animal tissue comprises
an instrument with an inner channel for carrying or supplying a fluid medium and at least one exit opening through which the fluid medium exits the inner channel and a target at an inner wall of the inner channel being in contact with the fluid medium or having the fluid medium flowing over the area with the target and an optical fiber having a free end opposite to the target providing laser radiation exiting at the free end of the optical fiber and being transmitted or aimed to or at the target at least partly through the fluid medium or through a space intervening between the free end of the optical fiber and the target which intervening space is in communication with the fluid medium and/or is filled with the fluid medium, wherein the laser radiation is selected such that as a result of optical breakdown at the target pressure pulses are generated within the fluid and/or the inner channel, the pressure pulses propagating in the fluid medium and exiting through the exit opening to the exterior.

Furthermore, according to the invention, an apparatus for removing epithelial cells (or: epithelial tissue) from the inside (or: the inwardly directed surface) of a lens-capsule bag of a human or animal eye, comprises
a) means for generating pressure pulses in a fluid medium within the lens-capsule bag, such that the fluid medium is adjacent to or covers the epithelial cells that are to be removed,
b) wherein the pressure pulses are so formed or selected that
b1) the epithelial cells can be or are detached from the wall of the lens-capsule bag by the impacting pressure pulses, and at the same time
b2) during removal of the epithelial cells no hole or comparable damage is produced in the wall of the lens-capsule bag, in particular by the pressure pulses.

Advantageous designs and further developments of the device in accordance with the invention will be apparent from the dependent claims.

DETAILED DESCRIPTION OF DRAWINGS AND EMBODIMENTS

In the following the invention is explained further with reference to exemplary embodiments.

Figure 1:
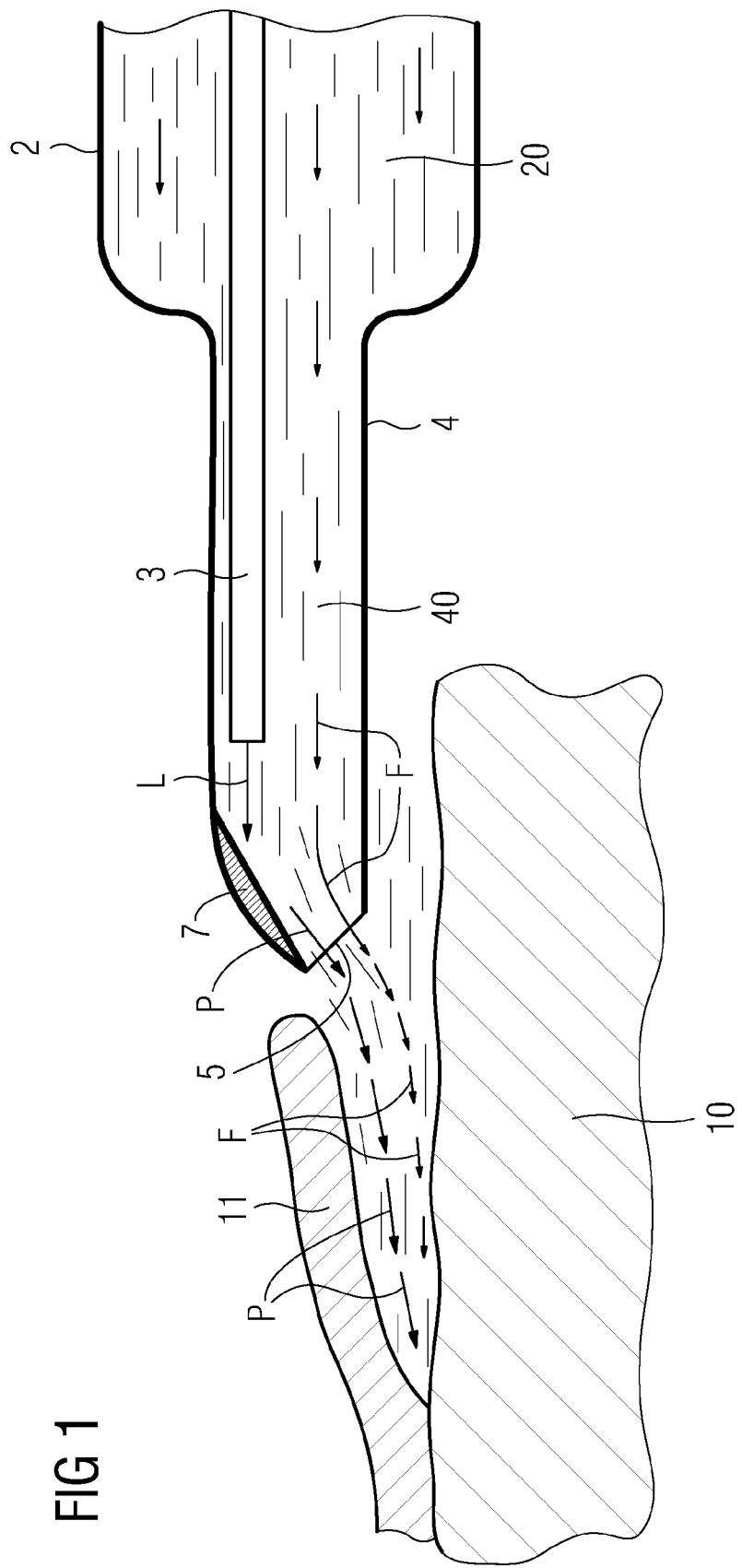
FIG. 1 depicts an exemplary device for removing and/or inhibiting unwanted molecular structures and/or cells from or at human or animal tissue in an operating state.

FIG. 1 depicts a device for removing and/or inhibiting unwanted molecular structures and/or cells from or at human or animal tissue in an operating state while removing the molecular structures and/or cells 11 from the tissue 10.

The device comprises a instrument 2 which is usually hand-held or a hand instrument or hand piece. The instrument 2 is hollow and surrounded by a closed side wall. In the inner space of the hollow instrument 2 a channel is formed which in the figure is used for supplying and guiding irrigation fluid F towards an opening 5 of the instrument 2 where the fluid F exits the instrument. The flow direction of the fluid F is indicated by arrows. At least towards its end the instrument 2 is formed like a needle or cannula or like a thin tube in an end section 4. The outer cross-section or diameter of the end section 4 is adapted to the space where the operation is to be performed and is usually smaller than in a section further away from the end section 4, typically the diameter is about 0.6 mm to 1.4 mm.

The inner channel of the instrument 2 carrying the fluid F in the end section 4 is designated by 40 and the inner channel before the channel 40, as seen in flow direction, is designated with 20. The inner channel 40 in the end section 4 opens, preferably at the very end, into the opening 5 which is formed in the wall of the instrument 2.

The channel 40 in the end section 4 has a smaller cross-section or diameter than the channel 20. Therefore, the fluid F is accelerated in the inner channel 40 of the end section 4 due to the smaller cross-section. Hence, the velocity and fluid pressure of the fluid F exiting at the opening 5 increase thereby enhancing and supporting the effect of separating and lifting off the unwanted molecular structures and/or cells 11 from the tissue 10, the fluid F streaming in particular in the intermediate space between the molecular structures and/or cells 11 and the tissue 10.

For the removing of the undesired molecular structures and/or cells 11 pressure pulses P are formed in the fluid F and exit from the instrument 2 at the opening 5 and hit or impact on the unwanted molecular structures and/or cells 11 at the tissue 10. The propagation directions of the pressure pulses P are indicated by arrows although of course the form of the pulses P in time and space can vary and be quite complex, usually formed like shock waves.

The pressure pulses P are preferably generated within the instrument 2, in particular as shown in the end section 4 near the opening 5. For this purpose a target 7 is provided in the end section 4 at the inner wall of the channel 40 near the opening 5, which target 7 is irradiated or hit by laser pulses L exiting from an end of an optical light guide or optical fiber 3 opposite the target 7. By means of the laser pulses L and an optical breakdown effect known as such pressure pulses P are generated in the fluid F which also streams over the area of the wall where the target 7 is and propagate through the fluid F to the opening 5 and towards the unwanted molecular structures and/or cells 11. The pressure pulses F accelerate the fluid F and enhance the fluid pressure to a great extent.

The target 7 and preferably the whole wall of the instrument 2 at least in the end section 4 is preferably made of titanium or an alloy thereof. The optical fiber 3 is longitudinally arranged within the channels 40 and 20 and at the other end connected to a laser source (not shown). The channel 20 is in fluid-connection to a pump (not shown) providing the pressure for the flow of the fluid F in the instrument 2. To achieve sufficient pressure at the opening 5 or port, for instance pressure from a gravity bottle height of 1 m above the tissue to be worked on is sufficient to create enough fluid flow through the needle or end section 4. The flow of the fluid F keeps the target 7 and the opening 5 clean from any residual tissue etc. and thereby ensures safe operation of the instrument.

This instrument 2 as depicted in FIG. 1 and described can be used for the removal but also the inhibiting of any unwanted molecular structures and/or cells 11 from any human or animal tissue 10. However two preferred applications are, as a first application, the removing and/or inhibiting of epithelial cells in the eye lens capsule bag from or at the bag tissue in order to prevent proliferation and/or migration of epithelial cells causing secondary eye cataract and, as a second application, the removing and/or inhibiting of pathogenic microorganisms from mucosa or skin tissue such as nose or sinuses or other areas of the body in particular where other treatments are not effective.

Figure 2:
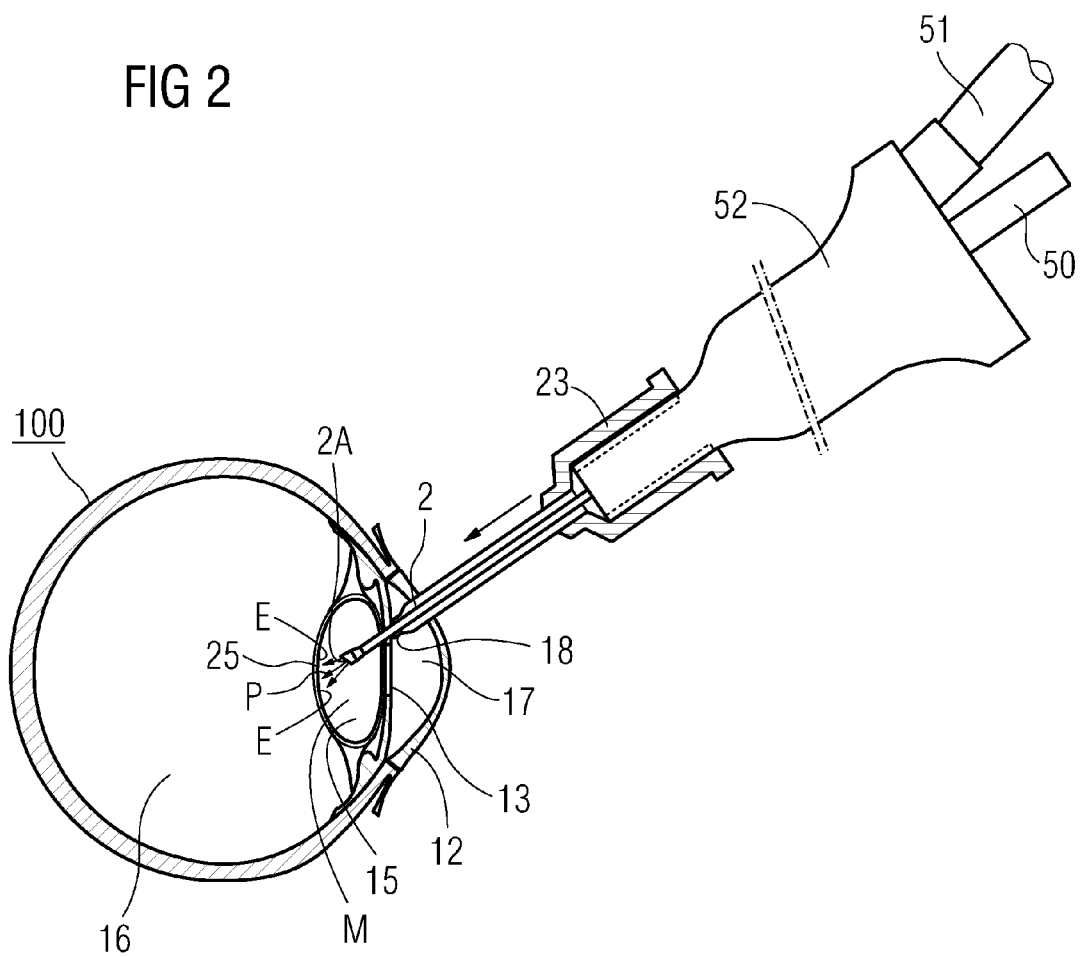
FIG. 2 depicts an exemplary handheld surgical instrument with a handpiece.

In the schematic drawing of FIG. 2 a handheld surgical instrument 2 with a handpiece 52 is shown during the operation for removal of epithelial cells E at the inside of the wall of the lens-capsule bag 25 of an eye 100. The lens-capsule bag 25 is filled with fluid medium M, for instance BSS, which is irrigated at the end 2A of the same instrument 2, or another irrigation instrument not shown, into the interior 15 of the lens-capsule bag 25 where previously the eye lens had been. Furthermore, in FIG. 2 there are shown the iris 14 which surrounds the pupil 13 and in front of the iris 14 and the pupil 13 the anterior chamber 17, which is delimited by the transparent cornea 12 to the front. The vitreous body of the eye 10 is depicted by 16. The instrument 2 is surrounded by a sleeve 23, for instance made of siloxane polymer, which reaches partly into the eye 10 through the incision in the cornea 12. At the handpiece 52 a feed line 50 is shown for supplying irrigation liquid such as BSS and an optical fiber or light guide 51 for transmitting laser light for generating pressure pulses P by the optical breakdown in a target material described above. The pressure pulses P are emitted at the end 2A of the instrument 2 and propagate through the medium M to the epithelial cells E. The pressure pulses P destroy or detach the epithelial cells E in the manner already described.

In the following further embodiments according to the invention are described.

A cataract operation, as a rule, comprises the following procedural steps:

First a surgical instrument, for instance a cannula, is used to open the front of the capsule bag, as a rule producing an opening that measures 4.5 to 5.5 mm (a process sometimes called "capsulorrhexis"). Afterwards, two incisions are made in the cornea, as a rule on opposite sides, in particular at the limbus, for a photolytic laser handpiece on one side and an irrigation handpiece on the other. By introducing a flushing fluid, e.g. BSS, the lens of the eye is detached from the capsule bag and hence mobilised (hydrodisection). By means of the irrigation instrument a flushing fluid, in general likewise BSS, is filled into the capsule bag and builds up a pressure that in particular prevents the back wall of the capsule bag from coming too close to the laser handpiece, while simultaneously cleaning the capsule bag.

By means of a laser handpiece or instrument, which for example can be a laser handpiece from the firm of A.R.C. Laser GmbH as mentioned above or can be constructed according to the documents U.S. Pat. No. 5,324,282 A or U.S. Pat. No. 5,906,611 A cited above, the lens of the eye is successively broken down photolytically by laser pulses striking a target and thereby producing shock waves, and sucked away. In this procedure the eye lens, in particular its nucleus, which is treated at the end of the procedure, can be moved by means of the irrigation tool so as to optimise its position relative to the laser handpiece. By means of a plurality of laser pulses and the shock waves thereby triggered, the tissue of the lens is broken down piece by piece and the individual tissue fragments can be sucked away through the laser handpiece by means of the pump. Subsequently, after the natural eye lens has been completely removed, an artificial lens is inserted into the capsule bag. The surgeon works with both instruments, one in each hand (bimanual technique).

According to one aspect of the invention, either before the artificial lens has been inserted or preferably after insertion of the artificial lens, which then closes off the opening in the front part of the capsule bag that was produced by the capsulorrhexis, epithelial cells are cleaned out of the inside of the capsule bag by removal from the wall of the lens-capsule bag by means of pressure pulses and preferably flushing off with the flushing liquid such as BSS.

For this purpose, in one preferred embodiment the instrument 2 shown in the figure can be used in the manner already described. In another embodiment a modified photolysis device from A.R.C. GmbH can be used to produce the pressure pulse for detaching or removing or forcing away the epithelial cells. In this case the same laser handpiece can be used as was used for explantation of the eye lens. However, in one embodiment no low pressure is produced in the aspiration channel, i.e. the pump is not connected to the laser handpiece. This measure serves to adapt the properties of the laser apparatus, so that instead of being directed towards destruction of the lens tissue they are made suitable for the more sensitive situation of removing epithelial cells from the capsule bag. In particular, it is necessary to prevent the device and the introduction of pressure pulses into the capsule bag from damaging the wall of the capsule bag.

That is, the wall of the capsule bag is relatively thin. As a result, after the natural eye lens has been removed, the lens-capsule bag cannot retain its shape, so that even after the flushing fluid has been introduced the capsule bag may nevertheless collapse at least partially, so that there is a risk of damage by the laser handpiece (instrument) used to remove the epithelial cells. However, it has been found that the relatively strong shock waves or pressure pulses generated by the A.R.C. laser handpiece are as a rule harmless to the capsule-bag wall when the tension in the latter is sufficiently reduced, so that it can yield to the pressure by changing its shape. Therefore the capsule wall should be prevented from being under tension, or to a certain extent stiff, when it is struck by the shock wave for removing or forcing away the epithelial cells. Accordingly, a considerable danger would arise if the aspiration function of the laser apparatus were turned on or left activated and the capsule-bag wall were pulled against the opening of the handpiece and then, while it is in this state, the shock were to impact against the capsule-bag wall. Furthermore, even on account of the low pressure used for aspiration the capsule-bag wall could be sucked in so as to produce a tear or an opening in it.

In order to avoid any complications, irrigation is provided through the laser handpiece in particular by using the channel which was used before for aspiration during removal of the natural eye lens. Aspiration is not necessary any more during this step of removal of epithelial cells as these can also be washed out with the fluid through the incisions.

In general the pulse repetition rate for the laser pulses, i.e. the number of laser pulses applied per unit time, for instance per second, is kept so low that after a laser pulse and the shock wave thereby produced have occurred, the capsule-bag wall can swing and move back into a relaxed state before the next laser pulse and associated shock wave, so that when the next laser pulse arrives it is not still in the deformed position in which it is under (maximal) tension and hence susceptible to tearing. That is, the capsule bag should, so to speak, be able to oscillate along with the repeated pressure pulses.

In initial experiments employing the modified A.R.C. laser device, i.e. without use of an aspiration means, it proved possible with the Nd-YAG laser present in the device, with laser light at the wavelength 1,064 nm, to remove lens epithelial cells such as are present in the capsule bag completely from substrates to which they had been applied, e.g. plastic substrates or millipore substrates for cultures.

A shock wave generated by a single laser pulse with pulse energy 7 mJ caused epithelial cells to be removed in a region having the following areas, given the following distances between the cells and the tip of the laser handpiece.

| Distance: epithelial cells to laser tip | Area from which epithelial cells removed |
|---|---|
| 1 mm | 6.3 mm$^2$ |
| 1.5 mm | 5.9 mm$^2$ |
| 2 mm | 7.2 mm$^2$ |
| 2.5 mm | 6.2 mm$^2$ |
| 3 mm | 5.3 mm$^2$ |
| 4 mm | 4.3 mm$^2$ | with an angle of incidence equal to 45°, and

| Distance: epithelial cells to laser tip | Area from which epithelial cells removed |
|---|---|
| 1 mm | 7.6 mm$^2$ |
| 1.5 mm | 6.7 mm$^2$ |
| 2 mm | 7.5 mm$^2$ |
| 2.5 mm | 6.8 mm$^2$ |
| 3 mm | 7.0 mm$^2$ |
| 4 mm | 1.3 mm$^2$ | with an angle of incidence equal to 90°.

Therefore in the first measurement series the cleared area obtained with a distance of 1 mm was almost approximately 6.5 mm$^2$, whereas with the larger distance of 4 mm the area in which the epithelial cells were removed was reduced by about 20 percent.

When the laser pulse energy was raised to 10 mJ, the following measured values were obtained:

| Distance: epithelial cells to laser tip | Area from which epithelial cells removed |
|---|---|
| 1 mm | 10.7 mm$^2$ |
| 1.5 mm | 12.1 mm$^2$ |
| 2 mm | 10.3 mm$^2$ |
| 2.5 mm | 7.5 mm$^2$ |
| 3 mm | 9.6 mm$^2$ |
| 4 mm | 7.9 mm$^2$ | with an angle of incidence equal to 45°, and

| Distance: epithelial cells to laser tip | Area from which epithelial cells removed |
|---|---|
| 1 mm | 7.0 mm$^2$ |
| 1.5 mm | 6.0 mm$^2$ |
| 2 mm | 5.7 mm$^2$ |
| 2.5 mm | 7.1 mm$^2$ |
| 3 mm | 7.0 mm$^2$ |
| 4 mm | 5.5 mm$^2$ | with an angle of incidence equal to 90°.

When the pulse energy was 10 mJ the ablation region, in which the epithelial cells were completely removed, was about 11 mm$^2$ for a distance between cells and laser-handpiece tip of 1 mm. For a distance of 4 mm from laser-handpiece tip to the cells, the area in which epithelial cells were removed was reduced by about 60 percent.

Even if measurement errors (standard deviations) are taken into account, a dependence of area on distance can be inferred that is not necessarily such that a decrease in the ablation area is the consequence of increasing distance and hence reduced pressure of the pressure wave. In each case there is at least one local maximum, for example in the region of a distance of 1.5 mm to 2 mm. Furthermore, a dependence on pulse energy and angle of incidence can be discerned, such that a higher pulse energy need not necessarily lead to a larger ablation area.

The measured pressure of the pressure pulses decreased with distance from the laser tip, as expected, and was for example between 190 bar at 1 mm distance and 20 bar at 4 mm distance (for 12 mJ laser-pulse energy).

At both levels of pulse energy (7 mJ and 10 mJ) the removal of the cells from the substrate surface was complete, and the ablation zone had sharp edges. Similar results were obtained with cell-culture substrates having flexible membranes with biomechanical properties resembling those of the capsule bag.

It was also found out that even when the pulse energy was reduced to 5 mJ or less down to 1 mJ per laser pulse there still a considerable reduction of proliferation and migration of epithelial cells and thus a significantly reduced risk of secondary cataract although at least a portion of the epithelial cells remained at the lens-capsule bag. The remaining epithelial cells, although they looked intact under the microscope, were not able to grow, multiply or migrate any more and seemed to become pignotic or inactive, in some cases even forming a barriere for other or new epithelial cells which barriere could not be overcome.

Although these initial experiments were carried out with a modified version of the existing A.R.C. laser system, which is actually intended to be used for another purpose, and even with these experiments an extremely promising removal of epithelial cells was achieved, it would nevertheless be more advantageous to use improved instruments, specialized for the removal of epithelial cells.

For instance, it would of course be possible to employ other laser types such as gas lasers or solid lasers of every kind as well or in addition, in particular if the shock waves are still produced by laser pulses that strike a target but also with another kind of pulse generation; however, it is also conceivable to construct the instrument so that it is flexible and hence can be brought close enough to otherwise inaccessible sites that are difficult to reach by way of the opening in the front of the capsule bag. For example, the tip of the laser handpiece along with the target and the optical fibre for transmitting the laser pulses to the target could be integrated into an endoscope that is flexible, with which in addition an optical imaging is possible so that the treated sites in the lens-capsule bag can be visually monitored.

Furthermore, other instruments and devices for generating pressure pulses in the liquid within the capsule bag can also be used to detach the epithelial cells, for instance piezoelectric, in particular piezoceramic, devices or those that operate by spark discharge in the medium, or also generators of pressure shock waves or pressure pulses that comprise membranes driven electromagnetically or inductively, e.g. by way of a coil. The pressure-pulse generators can be disposed in the region of the instrument that is inserted into the capsule bag, or else outside of the capsule bag in a separate unit that is connected to the instrument by way of a transmission line.

For transmitting the laser pulses, electrical driving signals or the pressure pulses themselves, the instrument is connected to a supply and driving unit by way of a tube or a cable through which the transmission lines pass. In this case the instrument and the tube are discarded after an operation, i.e. they are single-use products.

The repetition rate of the pressure pulses in the device is in particular limited, preferably already in the operating unit, to maximally 10 Hz, i.e. 10 pulses per second, in particular to at most 4 Hz. In principle, however, higher frequencies are also possible. No low-frequency limitation is required, and pulse repetition rates can be set to 1 Hz or below. The pressure pulses can be shock waves or pressure waves or also pressure currents or jets that are associated with the transport of material.

The frequency spectrum of the pressure wave prior to the generation of a shock wave by nonlinear effects can vary from the region of a few Hz into the region of 100 kHz, so that in addition to sonic oscillations in the audible range, ultrasonic waves or oscillations are possible. In the case of ultrasonic shock waves, in particular the means of producing ultrasonic shock waves that are known in the area of lithotripsy and other fields can be adapted to the requirements present here.

It is likewise conceivable, in particular in the case of low pulse or pressure energies and/or when the distances from the epithelial cells are small, to employ ultrasonic oscillators or platelets that operate at higher frequencies, namely ultrasonic frequencies, in order to clean or "polish" the inside of the capsule bag.

The energy or intensity of the pressure pulses for removal of epithelial cells from the lens-capsule bag is in general selected higher than for inhibiting the epithelial cells remaining at the lens-capsule bag, for instance at least 50 percent higher.

Basically the same method and device and/or pressure pulses described with respect to epithelial cells in the eye can also be used for removing or at least inhibiting pathogenic microorganisms such as bacteria or fungi or so called biofilms. The energy for removing biofilms or microorganisms is usually chosen to be higher that in the case of removal of epithelial cells in the eye, typically between 10 mJ to 25 mJ, in particular 12 mJ and 15 mJ, for the laser pulse energy. The irrigation liquid by its liquid pressure, which is preferably increased by diminishing the cross-section in the instrument in acts, in addition to the effect of the pressure pulses, as a separator for separating the biofilm from the tissue.

The invention claimed is:

1. A method for preventing a secondary cataract after a cataract operation, comprising:
   A) supplying a fluid medium to epithelial cells;
   B) generating pressure pulses in a fluid medium to impact the epithelial cells within a lens-capsule bag of an eye; and
   C) preventing at least one of proliferating or migrating of epithelial cells at an inside of the lens-capsule bag by at least one of detaching epithelial cells from a wall of the lens-capsule bag and inhibiting epithelial cells remaining on the wall of the lens-capsule bag by impacting pressure pulses;
   D) wherein the pressure pulses produce no hole in the wall on lens-capsule bag during detaching or inhibiting of the epithelial cells;
   E) wherein a pulse repetition rate of the pressure pulses is at most 4 pulses per second to allow a tissue of the lens-capsule bag, after a pressure pulse, to relax and enter a low-tension state by a time a next pressure-pulse occurs; and
   F) wherein the pressure pulses are generated by irradiating a target with laser radiation and causing a shock wave by optical breakdown generated by absorption at a target material, and the laser radiation is pulsed, with a pulse duration between 5 and 20 ns and with a pulse energy between 1 and 20 mJ, such that each laser pulse generates at least one pressure pulse.

2. The method according to claim 1, wherein a maximal pressure value of the pressure pulses at a distance of 0.5 mm is from 50 to 1,000 bar.

3. The method according to claim 1, further comprising removing epithelial cells by generating pressure pulses at a distance of about 1 mm to practically completely remove epithelial cells from the tissue in an area of about 0.1 to about 12 mm².

4. The method according to claim 1, further comprising removing epithelial cells by generating pressure pulses at a distance of about 4 mm to practically completely remove epithelial cells from the tissue in an area that is about 10% to about 80% smaller than when the distance is 1 mm, at the same pulse energy.

5. The method according to claim 1, wherein the pulse repetition rate of the pressure pulses is at most 2 pulses per second.

6. The method according to claim 1, wherein the pulse repetition rate of the pressure pulses is at most 1 pulse per second.

7. The method according to claim 1, further comprising generating a plasma by at least one pressure-pulse generator wherein the plasma generates at least one pressure pulse in the fluid medium.

8. The method according to claim 1, further comprising providing an instrument comprising an inner channel and at least one exit opening and a target at an inner wall of the inner channel, and an optical fiber comprising a free end opposite to the target.

9. The method according to claim 8, further comprising providing the fluid medium through the inner channel and exiting the at least one exit opening; and providing laser radiation through the fluid medium in the optical fiber to the epithelial cells.

10. The method according to claim 9, further comprising selecting the laser radiation to generate pressure pulses within the fluid medium and directing the pressure pulses to the epithelial cells.

11. The method according to claim 8, further comprising accelerating the fluid medium by providing the instrument with a reduced cross-section of the inner channel in an end section.

12. A method for removing biofilms, comprising:
A) supplying a fluid medium to the biofilms;
B) generating pressure pulses in a fluid medium to impact the biofilms on a mucosa tissue; and
C) detaching the biofilms from the mucosa tissue by impacting pressure pulses;
D) wherein the pressure pulses produce no hole in a wall of the mucosa tissue;
E) wherein a pulse repetition rate of the pressure pulses is at most 4 pulses per second to allow the mucosa tissue, after a pressure pulse, to relax and enter a low-tension state by a time a next pressure-pulse occurs; and
F) wherein the pressure pulses are generated by irradiating a target with laser radiation and causing a shock wave by a breakdown of the mucosa tissue generated by absorption at a target material, and the laser radiation is pulsed, with a pulse duration between 5 and 20 ns and with a pulse energy between 10 and 25 mJ, such that each laser pulse generates at least one pressure pulse.

13. The method according to claim 12, wherein the biofilms comprise pathogenic microorganisms.

14. The method according to claim 13, wherein the pathogenic microorganisms comprise bacteria.

15. The method according to claim 13, wherein the pathogenic microorganisms comprise fungi.

16. The method according to claim 12, wherein a maximal pressure value of the pressure pulses at a distance of 0.5 mm is from 50 to 1,000 bar.

17. The method according to claim 12, wherein the pulse repetition rate of the pressure pulses is at most 2 pulses per second.

18. The method according to claim 12, further comprising generating a plasma by at least one pressure-pulse generator wherein the plasma generates at least one pressure pulse in the fluid medium.

19. The method according to claim 12, further comprising providing an instrument comprising an inner channel and at least one exit opening and a target at an inner wall of the inner channel, and an optical fiber comprising a free end opposite to the target.

20. The method according to claim 19, further comprising providing the fluid medium through the inner channel and exiting the at least one exit opening; and providing laser radiation through the optical fiber to the biofilms through the fluid medium.

21. The method according to claim 20, further comprising selecting the laser radiation to generate pressure pulses within the fluid medium and directing the pressure pulses to the biofilms.

22. The method according to claim 19, further comprising accelerating the fluid medium by providing the instrument with a reduced cross-section of the inner channel in an end section.

23. A method for preventing or reducing proliferation or migration of epithelial cells at the inside of a lens-capsule bag of a human or an animal eye, the method being carried out during or after a cataract operation at the eye to reduce a risk of a secondary cataract, the method comprising:
A) supplying a fluid medium so that the fluid medium is adjacent to or covers epithelial cells;
B) generating pressure pulses in the fluid medium within the lens-capsule bag, which pressure pulses impact on the epithelial cells; and
C) detaching epithelial cells from a wall of the lens-capsule bag and/or inhibiting epithelial cells which remain at the wall of the lens-capsule bag by the impacting pressure pulses, so that the detached or inhibited epithelial cells are prevented from proliferating or migrating at the inside of the lens-capsule bag;
D) wherein the pressure pulses are so formed or selected that, during detaching or inhibiting of the epithelial cells no hole is produced in the wall of the lens-capsule bag by the pressure pulses;
E) wherein at least one of a pulse repetition rate of the pressure pulses and an adjustable range of the pulse repetition rate of the pressure pulses is selected or adjusted in such a way that a tissue of the lens-capsule bag, after a pressure pulse, relaxes and enters a low-tension state by a time a next pressure-pulse occurs and wherein the pulse repetition rate of the pressure pulses is at most 4 pulses per second; and
F) wherein pressure pulses are generated by irradiating a target with laser radiation and causing a shock wave by optical breakdown generated by absorption at a target material, wherein the laser radiation is pulsed, with a pulse duration between 5 ns and 20 ns and with a pulse energy between 1 and 20 mJ, such that each laser pulse generates at least one pressure pulse.

* * * * *